US010203299B2

(12) United States Patent
Bosio et al.

(10) Patent No.: US 10,203,299 B2
(45) Date of Patent: Feb. 12, 2019

(54) CIRCUIT AND METHOD FOR CONTROLLING A SINGLE-CELL LINEAR OXYGEN SENSOR

(71) Applicant: MAGNETI MARELLI S.p.A., Corbetta (IT)

(72) Inventors: Matteo Bosio, Bologna (IT); Piero Maria Carbonaro, Turin (IT); Fausto Calcagno, Santena (IT)

(73) Assignee: MAGNETI MARELLI S.p.A., Corbetta (IT)

( * ) Notice: Subject to any disclaimer, the term of this patent is extended or adjusted under 35 U.S.C. 154(b) by 288 days.

(21) Appl. No.: 15/238,068

(22) Filed: Aug. 16, 2016

(65) Prior Publication Data

US 2017/0052141 A1 Feb. 23, 2017

(30) Foreign Application Priority Data

Aug. 17, 2015 (IT) .................. 102015000044967

(51) Int. Cl.

| | |
|---|---|
| *G01N 27/406* | (2006.01) |
| *G01N 27/407* | (2006.01) |
| *F01N 13/00* | (2010.01) |
| *F01N 13/08* | (2010.01) |
| *F02M 35/10* | (2006.01) |
| *G01N 27/409* | (2006.01) |

(52) U.S. Cl.
CPC ....... *G01N 27/4065* (2013.01); *F01N 13/008* (2013.01); *F01N 13/08* (2013.01); *F02M 35/10393* (2013.01); *G01N 27/407* (2013.01); *G01N 27/409* (2013.01); *G01N 27/4067* (2013.01); *F01N 2900/1402* (2013.01)

(58) Field of Classification Search
CPC .. G01N 27/4065; G01N 27/409; G01N 27/41; G01N 27/4067; F01N 13/008; F01N 13/08; F01N 2900/1402; F02M 35/10393
USPC .................. 73/23.32, 1.06, 114.71–114.73
See application file for complete search history.

(56) References Cited

U.S. PATENT DOCUMENTS

2007/0215470 A1 9/2007 Kawase et al.

OTHER PUBLICATIONS

Search Report and Written Opinion issued by the Italian Patent Office for Italian Patent Application No. IT UB2015316; dated Apr. 25, 2016.

*Primary Examiner* — Robert R Raevis
(74) *Attorney, Agent, or Firm* — Howard & Howard Attorneys PLLC

(57) ABSTRACT

A control circuit for a single-cell linear oxygen sensor having a first and a second electrical terminals on which a first voltage and respectively a second voltage are present, wherein a cell current between the first and second electrical terminals is indicative of a detected oxygen concentration, and wherein the control circuit generates a biasing voltage between the first and the second electrical terminals with a preset pattern as a function of the cell current. The circuit envisages: a transresistance block, coupled to the second electrical terminal to generate a processed voltage as a function of the cell current and based on the preset pattern; and an adder stage, coupled to the transresistance block and to the second electrical terminal, to perform a sum between the processed voltage and the second voltage, to generate the first voltage for the first electrical terminal of the linear oxygen sensor, so that the biasing voltage has the preset pattern as a function of the cell current.

19 Claims, 5 Drawing Sheets

US 10,203,299 B2

1

CIRCUIT AND METHOD FOR CONTROLLING A SINGLE-CELL LINEAR OXYGEN SENSOR

The present invention relates to a circuit and method for controlling a linear oxygen sensor, in particular of a single-cell type.

BACKGROUND OF THE INVENTION

Linear oxygen sensors are known, the so-called UEGO sensors (Universal Exhaust Gas Oxygen sensor), used, for example, in internal combustion engines for measuring the concentration of oxygen in the gases in a discharge and/or intake conduit, and thus obtaining information about the air/fuel (A/F) ratio at the discharge and/or intake.

These linear oxygen sensors are based on the use of electrolytic sensing cells, for example including zirconium dioxide ($ZrO_2$), which are sensitive to the oxygen ions, and which generate suitable electrical signals depending on the quantity of oxygen present, when they come into contact with the gases.

In particular, linear oxygen sensors are known that use two electrolytic cells, generally defined as "pumping cell" and "sensing cell", and linear oxygen sensors that envisage instead the use of a single electrolytic sensing cell.

For example, EP 1 001 261 A1, in the name of the present Applicant, discloses a control device, of an integrated microcontroller type, for a double cell linear oxygen probe.

Single-cell linear oxygen sensors may sometimes be preferable, for example for reducing the costs, size and circuit complexity of the associated control device.

As shown in the schematic sections in FIGS. 1a and 1b, a linear oxygen sensor, of a single-cell type, indicated in general by 1, comprises:

an electrolytic layer 2, including, for example zirconium dioxide, $ZrO_2$;

a first and a second electrode 3a, 3b, in contact with the electrolyte layer 2, set on opposite sides in relation to the same electrolyte layer 2, and defining a first (positive pole) and, respectively, a second (negative pole) electrical terminal of the linear oxygen sensor 1;

a diffusion layer 4, above the first electrode 3a and in contact, during operation, with the gases whose oxygen concentration is desired to be measured, for example discharge gases (the second electrode 3b being placed in contact with an environment containing a reference air).

The linear oxygen sensor 1 furthermore comprises: a reference air duct 5, defining the aforesaid environment in contact with the second electrode 3b; and a heating element 6, set below the reference air duct 5, and suitably driven by applying an electrical quantity, to bring the electrolytic sensing cell to a suitable temperature (for example equal to 700°).

During operation, the cell current $I_p$ that flows between the electrical terminals of the linear oxygen sensor 1 (denoted schematically with a current generator 7 in FIG. 1b), across which a biasing voltage $\Delta V$ of a suitable value is set (FIG. 1b shows a voltage generator $\Delta V$ in series with a resistor 8), is indicative of the oxygen percentage; this cell current $I_p$ is consequently indicative of the air/fuel ratio A/F, as illustrated by way of example in FIG. 2.

It is known that, in the field of controlling linear oxygen sensors, the applied electrical quantities (in particular, the biasing voltage between the associated electrical terminals) are required to be within given (upper and lower) thresholds; exceeding (above or below) these thresholds may in fact

2 cause the so-called phenomenon of "blackening" of the electrolyte, which is potentially damaging to the sensor or, in any case, sufficient to compromise its proper operation.

Furthermore, in the case of the previously illustrated single-cell linear oxygen sensor 1, the voltage applied between the corresponding electrical terminals is required to have a given relationship with the cell current $I_p$, with a suitable variation in correspondence with the variation of the same cell current $I_p$.

SUMMARY OF THE INVENTION

The aim of the present invention is to provide a solution for controlling a single-cell linear oxygen sensor, with a simple and inexpensive configuration, which offers good electrical performance.

According to the present invention, a control circuit for controlling a linear oxygen sensor, and a corresponding control method, are therefore provided, as defined in the accompanying claims.

BRIEF DESCRIPTION OF THE DRAWINGS

For a better understanding of the present invention, a preferred embodiment will now be described, by way of example, which is not limiting, with reference to the accompanying Figures, wherein.

DETAILED DESCRIPTION OF THE INVENTION

Figure 3:
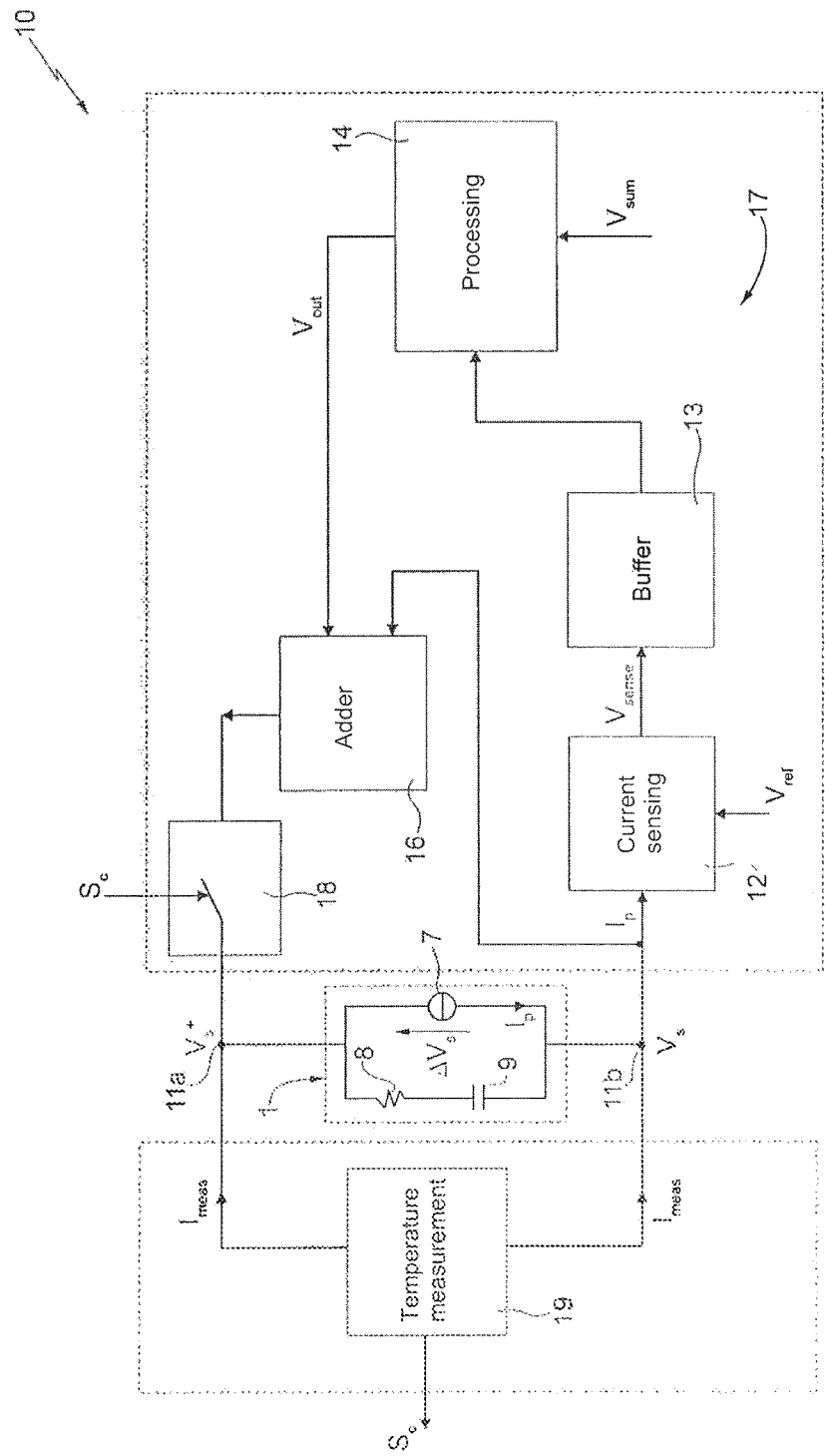
FIG. 3 is a block diagram of a control circuit for a linear oxygen sensor, according to one embodiment of the present solution.

As shown in FIG. 3, one aspect of the present solution envisages implementing a control circuit, purely analog in this embodiment, indicated as a whole by 10, for the biasing of a single-cell linear oxygen sensor, again denoted by 1.

Figure 1A:
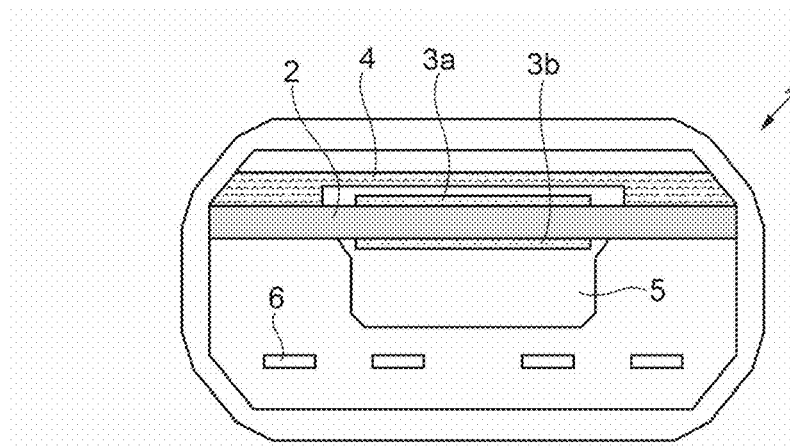
FIGS. 1a-1b are schematic section diagrams, with different levels of detail, of a known type of single-cell linear oxygen sensor.
Figure 1B:
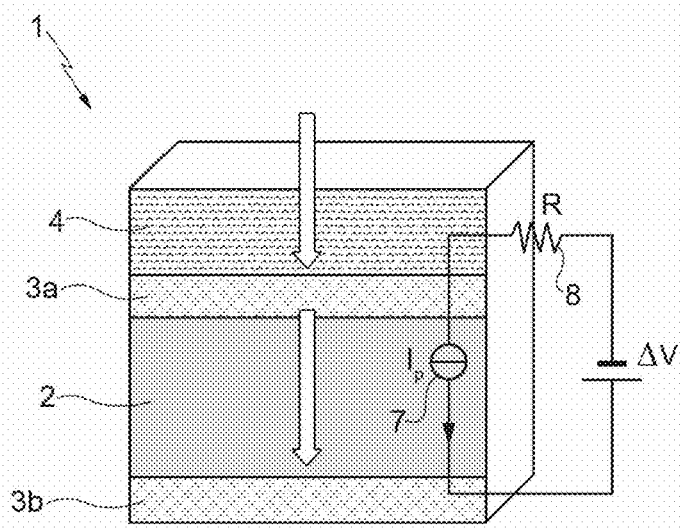
Figure 2:
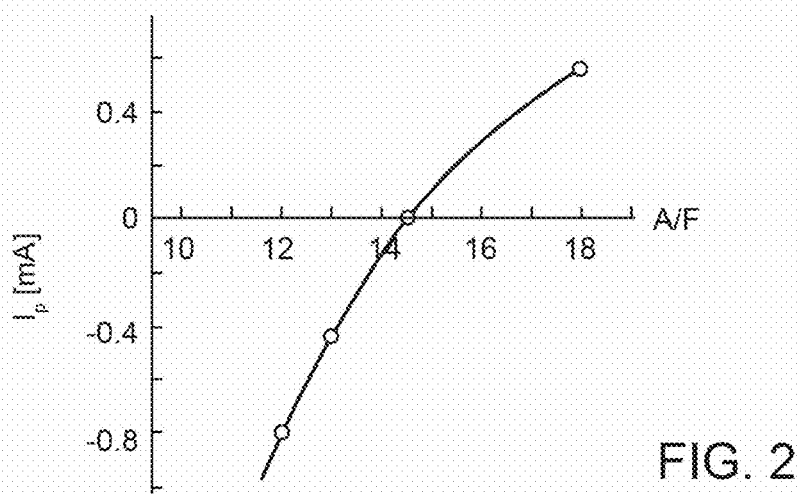
FIG. 2 is a plot relating to electrical and oxygen concentration quantities in the sensor of FIGS. 1a, 1b.

The linear oxygen sensor 1 may be structured in a similar way to what was previously discussed, with reference to FIGS. 1a-1b, and is schematised, from the circuit point of view, with the current generator 7, which is connected between the first and second electrical terminals, denoted here with 11a and 11b; and the series connection of resistor 8 and capacitor 9 that are connected between the same first and second electrical terminals 11a, 11b.

In particular, the control circuit 10 is configured to generate a suitable biasing voltage, indicated here with $\Delta V_s$, between the electrical terminals 11a and 11b of the linear oxygen sensor 1, as a function of the value of the cell current $I_p$ supplied by the same linear oxygen sensor 1 based on the detected oxygen concentration, respecting the pattern and minimum and maximum thresholds envisaged by design, for the proper operation of the same linear oxygen sensor 1.

During operation, a first voltage $V_s^+$ is present on the first electrical terminal 11a of the linear oxygen sensor 1, which is assumed for example to be positive, while a second voltage $V_s^-$ is present on the second electrical terminal 11b of the linear oxygen sensor 1 (for example, this is also positive, and lower compared to the first voltage $V_s^+$); the biasing voltage $\Delta V_s$ is given by the difference between the first and second voltages $V_s^+$, $V_s^-$: $\Delta V_s = V_s^+ - V_s^-$.

In detail, the control circuit 10 comprises:

a sensing stage 12, coupled to the second terminal 11b of the linear oxygen sensor 1, configured to supply a sense voltage $V_{sense}$, indicative of the value of the cell current $I_p$, referred to a reference voltage $V_{ref}$, having a suitable value, for example equal to 3.8 V; in particular, the sense voltage $V_{sense}$ increases or decreases (according to the direction of the cell current $I_p$) proportionally to the same cell current $I_p$;

a buffer stage 13, having the function of impedance decoupling, connected to the output of the sensing stage 12;

an amplifier stage 14, coupled to the output of the sensing stage 12 by the buffer stage 13, configured to process the sense voltage $V_{sense}$, by applying a suitable gain k and offset voltage $V_{sum}$, as subsequently described in greater detail, generating a processed voltage $V_{out}$;

an adder stage 16, which receives the second voltage $V_s^-$ on the second electrical terminal 11b of the linear oxygen sensor 1, at a first input, and the processed voltage $V_{out}$, at a second input, and performs a weighted sum thereof to compensate the gain k previously applied by the amplifier stage 14, thus generating the first voltage $V_s^+$ to be applied to the first electrical terminal 11a of the same linear oxygen sensor 1;

a selective-coupling stage 18, set between the output of the adder stage 16 and the first electrical terminal 11a, and configured to selectively couple the output of the adder stage 16 to the same first electrical terminal 11a, according to a control signal $S_c$; in particular, in correspondence with a first value of the control signal $S_c$ (for example high), the first voltage $V_s^+$ generated by the adder stage 16 is supplied to the first electrical terminal 11a of the linear oxygen sensor 1, while for a second value of the same control signal $S_c$ (for example low), the output of the adder stage 16 is brought to a high-impedance state, decoupled from the same first electrical terminal 11a.

Together, the sensing stage 12 and the amplifier stage 14 form a transresistance block, indicated as a whole with 17, designed to generate, as a function of the cell current $I_p$, a suitable value of the processed voltage $V_{out}$ (which determines the appropriate value of the first voltage $V_s^+$ on the first terminal 11a of the linear oxygen sensor 1, in relation to the second terminal 11b).

Figure 4A:
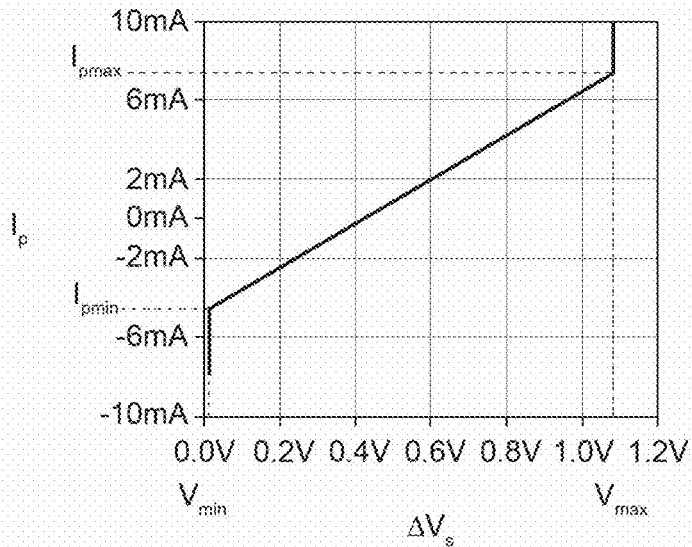
FIGS. 4a, 4b are plots of electrical quantities relating to the control circuit in FIG. 3.

In particular, as shown in FIG. 4a, the electrolytic sensing cell of the linear oxygen sensor 1 has a desired pattern, according to design, which links ("maps") the variation of the cell current $I_p$ to the biasing voltage $\Delta V_s$ applied between the terminals 11a, 11b.

In the shown example, as the cell current $I_p$ varies, this pattern for the biasing voltage $\Delta V_s$ envisages: a minimum voltage limit $V_{min}$, in the example, close to 0 V, for values of the cell current $I_p$ below a lower threshold $I_{pmin}$; a maximum voltage limit $V_{max}$, in the example, close to 1.2 V, for values of the cell current $I_p$ above an upper threshold $I_{pmax}$; and, between the minimum and maximum voltage limits $V_{min}$, $V_{max}$, a linear ramp pattern, with a preset slope.

Furthermore, for a null value of the cell current $I_p$ a non-null value of the biasing voltage $\Delta V_s$ is envisaged, in the example equal to about 0.4 V.

According to one aspect of the present solution, the gain k and the offset voltage $V_{sum}$ of the amplifier stage 14 are suitably selected to replicate the aforesaid desired (by design) pattern of the biasing voltage $\Delta V_s$, as the cell current $I_p$ varies.

In particular, for values of the cell current $I_p$ below the lower threshold $I_{pmin}$, or above the upper threshold $I_{pmax}$, the gain k is such that the amplifier stage 14 operates at the upper or lower saturation voltages (so-called "supply rails"); in other words, the amplifier stage 14 operates across all of its dynamics, with the processed voltage $V_{out}$ that cannot exceed the upper and lower saturation voltages.

Figure 4B:
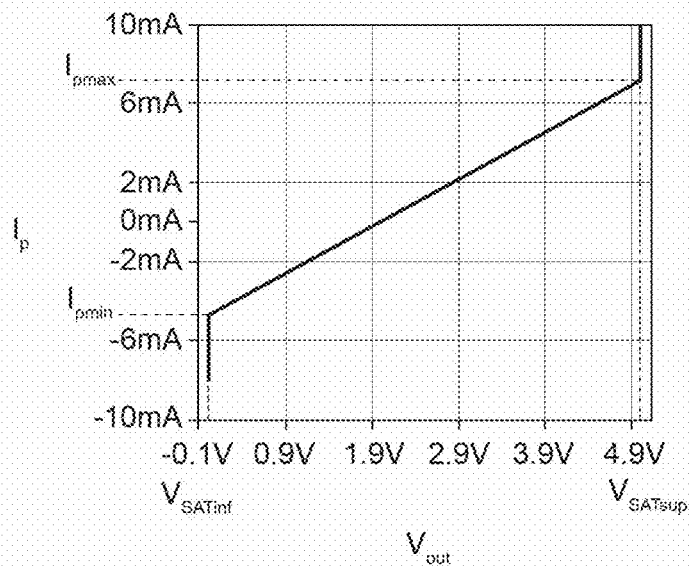

A possible pattern of the processed voltage $V_{out}$ is illustrated in FIG. 4b: the value of the processed voltage $V_{out}$ is comprised between the upper and lower saturation voltages, indicated here with $Vsat_{inf}$, $Vsat_{sup}$, and furthermore a non-null value of the same processed voltage $V_{out}$ corresponds to a null value of the cell current $I_p$.

In this way, the amplifier stage 14 ensures that the limits envisaged by design for the biasing voltage $\Delta V_s$ applied to the linear oxygen sensor 1 are respected. Furthermore, compensating the gain k applied by the amplifier stage 14, the adder stage 16 subsequently allows to obtain the desired value of the biasing voltage $\Delta V_s$, starting from the processed voltage $V_{out}$ supplied by the same amplifier stage 14.

According to a further aspect of the present solution, the selective coupling stage 18 is operable to decouple the linear oxygen sensor 1 from the control circuit 10, in certain operating conditions, in particular when it is desired to measure the operating temperature of the same linear oxygen sensor 1.

To measure this operating temperature, a measurement current $I_{meas}$ is injected into the linear oxygen sensor 1 and the corresponding resistance at the passage of the same measurement current $I_{meas}$ is measured; the resistance measurement is indicative of the temperature of the linear oxygen sensor 1.

In particular, to this end, a measurement stage 19 is coupled to the first and second electrical terminals 11a, 11b of the linear oxygen sensor 1, being configured to inject the measurement current $I_{meas}$, for example of an impulsive type, at the first and/or second electrical terminal 11a, 11b, and determine the resistance of the same linear oxygen sensor 1 (based on the drop in voltage caused by the same measurement current $I_{meas}$ between the electrical terminals 11a, 11b).

The measurement stage 19 is configured, furthermore, to generate the control signal $S_c$ for the selective coupling stage 18, suitably timed to perform the operation of temperature measurement. In particular, the selective coupling stage 18 is operated to decouple the linear oxygen sensor 1 from the control circuit 10, for a brief period of time, which is sufficient to measure the temperature, but is such as not to cause unwanted variations in the biasing conditions of the same linear oxygen sensor 1, as determined by the control circuit 10.

Figure 5:
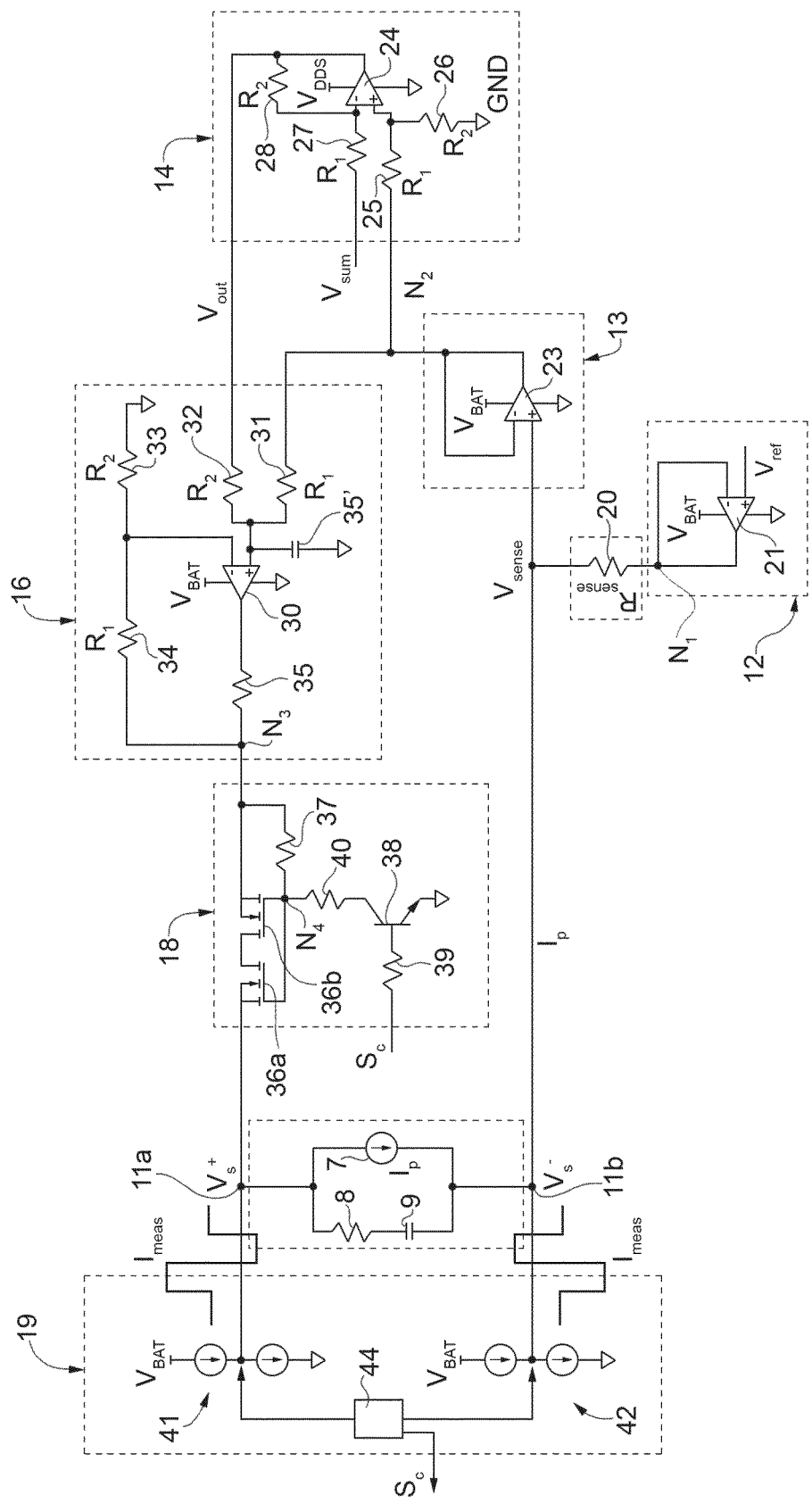
FIG. 5 is a more detailed circuit diagram of the control circuit in FIG. 3.

A possible embodiment of the control circuit 10 will now be described in further detail, with reference to FIG. 5.

The sensing stage 12 comprises in this case: a sensing resistor 20, having resistance $R_{sense}$, connected between the second electrical terminal 11b of the linear oxygen sensor 1 and a first internal node $N_1$; and a first buffer amplifier 21, which has a non-inverting input that receives the reference voltage $V_{ref}$, an inverting input connected to the output (in voltage-follower configuration), and the output connected to the first internal node $N_1$, on which it thus feeds-back the same reference voltage $V_{ref}$.

During operation, the cell current $I_p$ determines a drop in voltage on the sensing resistor 20 equal to $R_{sense} \cdot I_p$, so the sense voltage $V_{sense}$ is equal to:

$$V_{sense} = R_{sense} \cdot I_p + V_{ref}$$

and therefore proportional to the cell current $I_p$.

The buffer stage 13 comprises a second buffer amplifier 23, which has a non-inverting input connected to the second electrical terminal 11b of the linear oxygen sensor 1, an inverting input connected to the output (in voltage follower configuration), and the output connected to a second internal node $N_2$, on which it thus feeds-back the second voltage $V_s^-$ (coinciding with the sense voltage $V_{sense}$).

The amplifier stage 14 comprises an operational amplifier 24, having: a non-inverting input, connected to the second internal node $N_2$ via a first gain resistor 25, having resistance $R_1$, and also connected to a reference ground terminal GND via a second gain resistor 26, having resistance $R_2$; an inverting input, connected via a third gain resistor 27, in the example having resistance $R_1$, to an offset input, on which the offset voltage $V_{sum}$ is present, and also connected to the corresponding output via a fourth gain resistor 28, having resistance $R_2$; and the output providing the processed voltage $V_{out}$.

In a non-illustrated manner, the offset voltage $V_{sum}$ can be generated from the same reference voltage $V_{ref}$, for example by a resistive divider.

The processed voltage $V_{out}$ is thus given by the following expression:

$$V_{out} = k \cdot (V_{sense} - V_{sum})$$

wherein the gain k is defined by the values of the resistances $R_1$ and $R_2$ of the gain resistors: $k = R_2/R_1$.

The operational amplifier 24 furthermore receives a supply voltage $V_{DDS}$, for example equal to 5 V, whose value determines, in a known manner, the values of the corresponding upper and lower saturation voltages (supply rails) $Vsat_{inf}$, $Vsat_{sup}$.

The adder stage 16 comprises, in turn, an operational amplifier 30, having: a non-inverting input, connected to the second internal node $N_2$ via a fifth gain resistor 31, having resistance $R_1$, and also connected to the output of the operational amplifier 24 of the amplifier stage 14 via a sixth gain resistor 32, having resistance $R_2$; an inverting input, connected via a seventh gain resistor 33, in the example, having resistance $R_2$ to the ground terminal GND, and furthermore connected to a third internal node $N_3$ via an eighth gain resistor 34, having resistance $R_1$; and an output connected to the third internal node $N_3$ via a further resistor 35, for the purpose of protection in the case of short-circuit, and providing the first voltage $V_s^+$, for the first terminal 11a of the linear oxygen sensor 1.

The non-inverting input of the operational amplifier 30 is also connected to the ground terminal GND via a condenser 35', having "loop-compensation" functions to stabilise the control loop.

The first voltage $V_s^+$ is thus given by the following expression:

$$V_s^+ = \frac{1}{k} \cdot V_{out} + V_s^-.$$

The selective coupling stage 18 comprises: a first and a second switch element 36a, 36b (in the example made with a respective MOSFET transistor), connected in series between the third internal node $N_3$ and the first electrical terminal 11a of the linear oxygen sensor 1, and having control terminals connected to each other and to a fourth internal node $N_4$. The same fourth internal node $N_4$ is connected to the third internal node $N_3$ via a further resistor 37.

The selective coupling stage 18 further comprises a bipolar transistor 38, having a base terminal connected to a control input where it receives (from the measurement stage 19) the control signal $S_c$ through a resistor 39, a collector terminal connected to the fourth internal node $N_4$ via a resistor 40, and an emitter terminal connected to the ground terminal GND.

In the illustrated embodiment, the aforesaid measuring stage comprises: a first, bidirectional current generator 41, connected to the first electrical terminal 11a of the linear oxygen sensor 1, receiving a supply voltage $V_{BAT}$ (that also supplies the operational amplifiers 21, 23 and 30); and a second, bidirectional current generator 42, connected to the second electrical terminal 11b of the same linear oxygen sensor 1, receiving the supply voltage $V_{BAT}$.

The first and second current generator 41, 42 are operable to inject the measurement current $I_{meas}$, in the example, of an impulsive type, towards the first or second electrical terminal 11a, 11b of the linear oxygen sensor 1, said current being provided by a pair of consecutive impulses, with opposite polarity and a duration, for example, equal to 0 μs and an amplitude equal to +/−2.5 mA.

The measurement current $I_{meas}$ can be supplied alternatively in both directions, towards the respective electrical terminal 11a, 11b, or from the same electrical terminal 11a, 11b.

As indicated previously, the duration of the temperature measuring operation is such that it does not alter the biasing conditions and therefore the state of the electrolyte in the electrolyte layer 2 of the linear oxygen sensor 1.

The measuring stage 19 furthermore comprises a control unit 44, configured to drive the first and second current generator 41, 42 and furthermore to generate the control signal $S_c$ for the selective coupling stage 18, based on a same timing signal. In a manner not shown, the control unit 44 can also be operatively coupled to a high-level management unit, for example of the engine in which the linear oxygen sensor 1 is employed, from which it may receive suitable commands.

During operation, the control unit 44 is able to start the procedure for measuring the temperature of the linear oxygen sensor 1 by switching the control signal $S_c$; subsequently, the same control unit 44 drives the current generators 41, 42 to provide the measurement current $I_{meas}$ through the linear oxygen sensor 1, determining the temperature value based on the resistance measurement between the electrical terminals 11a, 11b of the same linear oxygen sensor 1.

Figure 6:
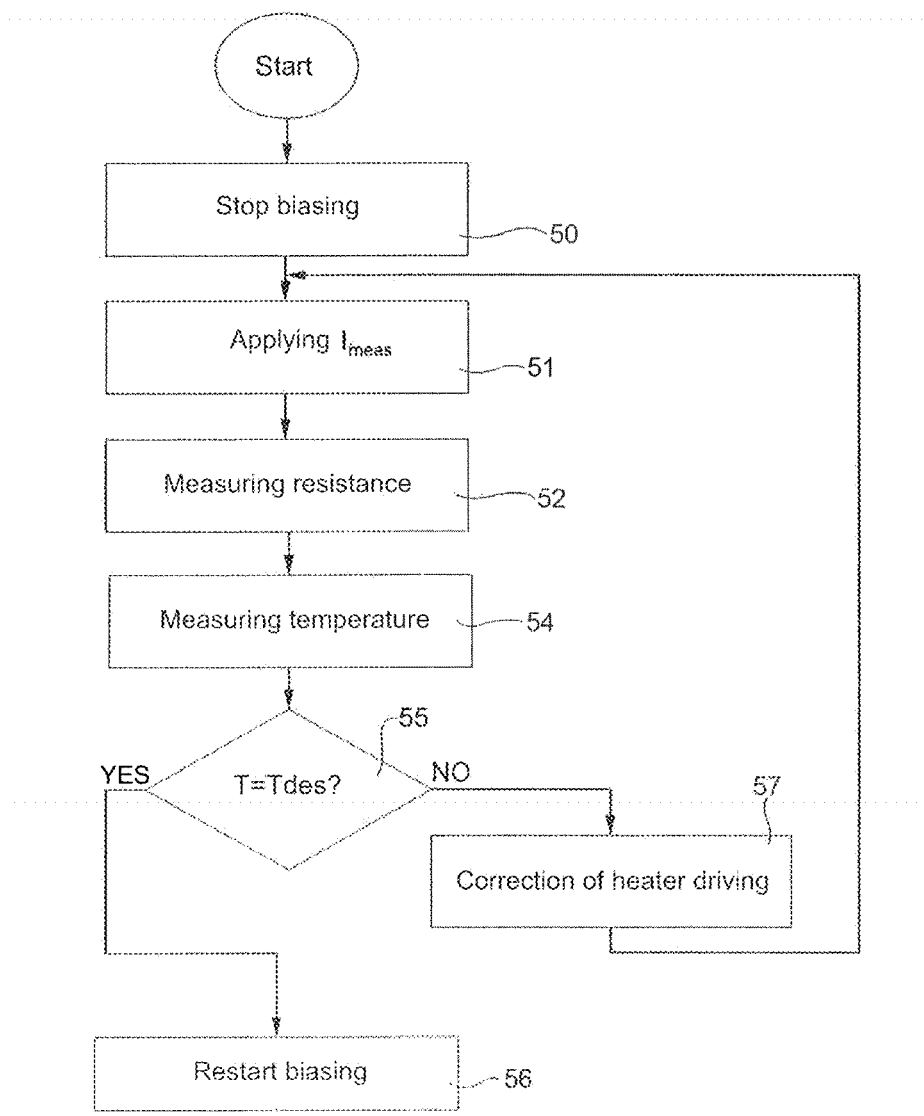
FIG. 6 is a flow diagram of control operations performed by the control circuit of FIG. 3.

In greater detail, and as illustrated in FIG. 6, the temperature measurement procedure implemented by the control unit 44 of the measuring stage 19, envisages, in a first step 50, switching of the first and second switch element 36a, 36b in the selective coupling stage 18 to decouple the control circuit 10 from the linear oxygen sensor 1 (in particular, both of the switches 36a, 36b are opened) and interrupt the biasing of the same linear oxygen sensor 1.

Subsequently, at step 51, the control unit 44 determines supply of the measurement current $I_{meas}$ through the linear oxygen sensor 1, driving the first and/or second current generator 41, 42.

The resistance of the linear oxygen sensor 1 is then measured, step 52, as a function of the drop in voltage between the corresponding electrical terminals 11*a*, 11*b* caused by the passage of the measurement current $I_{meas}$.

In this way, the control unit 44 determines the temperature value, as a function of the measured resistance, at step 54.

In a subsequent step 55, the control unit 44 may verify whether the previously determined temperature value T corresponds, or not, to a desired operating temperature $T_{des}$ for the linear oxygen sensor 1.

If verification is positive, no correction is made, and the control circuit 10 can subsequently be coupled again to the linear oxygen sensor 1, to supply the biasing voltage $\Delta V_s$ and continue the oxygen concentration sensing operations, step 56.

Otherwise, step 57, the drive current supplied to the heating element 6 of the linear oxygen sensor 1 can be suitably modified (see FIG. 1*a*), according to the difference between the temperature T and the desired operating temperature $T_{des}$.

It is possible to return from step 57 to step 51, in a iterative manner, for another check of the value of the temperature T, until the same temperature T reaches the desired value.

In particular, measurement of the temperature T of the linear oxygen sensor 1, and any correction of the drive quantities supplied to the heating element 6, can be carried out on a continuous basis, at fixed periodic intervals, or whenever required, in other words when it is suitable to monitor and update the value of the same temperature.

In a manner that is non-illustrated, but which is evident from the discussion, return from step 56 to step 50 (for a new measurement of the temperature T) occurs for example after a set waiting time, or after receiving from the high level management unit coupled to the control unit 44 a command to monitor the temperature.

The advantages of the proposed solution appear evident from the previous description.

In any case, it is again underlined that it allows effective biasing and effective control of a single-cell linear oxygen sensor, but with reduced circuit complexity and implementation costs.

The safety of the control circuit 10 is intrinsically guaranteed, since it is impossible for the biasing voltage to assume values, which are higher or lower than the limit values tolerable by the linear oxygen sensor 1 (in particular, thanks to the limited dynamics of the operational amplifier 24 of the processing stage 14).

The possibility of decoupling the control circuit of the linear oxygen sensor 1, when the relative operating temperature needs to be measured is particularly advantageous.

Advantageously, the control circuit 10, in the described embodiment being of a completely analog type, is able to cooperate with additional processing units (for example microprocessor units), which can be operatively coupled to the same linear oxygen sensor 1, for example to perform operations of reading and processing the data acquired and/or operations of diagnosing the operation of the same linear oxygen sensor 1. These processing units may be coupled to the same printed circuit board (PCB) in which the control circuit is formed 10.

Figure 7:
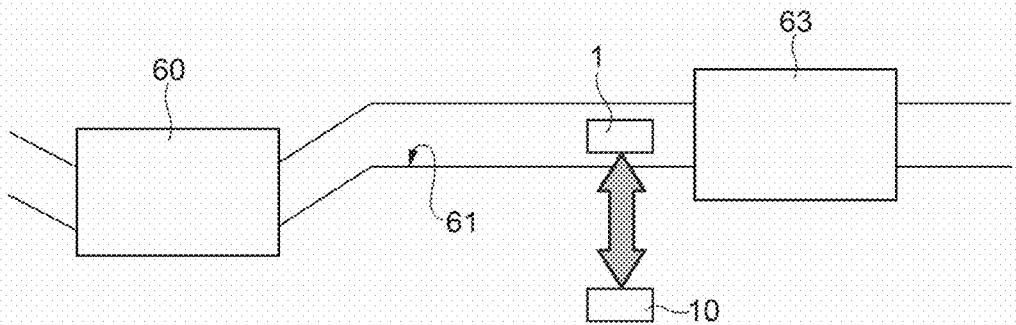
FIG. 7 schematically shows a portion of an internal combustion engine in which the linear oxygen sensor and the corresponding control circuit can be employed.

As shown schematically in FIG. 7, the described solution may advantageously be applied, for example in an internal combustion engine 60, to control a linear oxygen sensor 1, set inside a discharge conduit 61, for measuring the concentration of oxygen in discharge gases, and thus provide an indication of the A/F ratio.

In the illustrated example, the linear oxygen sensor 1 is, for example positioned before a catalyst 63, suitable for eliminating polluting substances present in the combustion gases, before the same gases are released into the environment; however, in a non-illustrated manner, the linear oxygen sensor 1 could equally be positioned downstream of the catalyst 63 (or positioned at an intake conduit of the internal combustion engine 60).

Finally, it is clear that modifications and variations can be made to what is described and illustrated here without departing from the scope of the present invention, as defined in the accompanying claims.

In particular, it is evident that the control circuit 10 may implement different curves that describe the desired pattern (according to design), which links the variation of the cell current $I_p$ to the biasing voltage $\Delta V_s$ between the electrical terminals 11*a*, 11*b* of the linear oxygen sensor 1, for example in terms of a different slope of the linear ramp pattern, and/or a different minimum voltage limit $V_{min}$, and/or a different maximum voltage limit $V_{max}$.

Furthermore, it is again underlined that the control circuit may be employed for controlling single-cell linear oxygen sensors in various applications, also in ones different from the previously-referenced internal combustion engine.

The invention claimed is:

1. A control circuit (10) for a single-cell linear oxygen sensor (1) having a first (11*a*) and a second (11*b*) electrical terminals on which a first voltage ($V_s^+$) and, respectively, a second voltage ($V_s^-$) are designed to be provided, wherein a cell current ($I_p$) between said first (11*a*) and second (11*b*) electrical terminals is indicative of a detected oxygen concentration, said control circuit (10) being configured to generate a biasing voltage ($\Delta V_s$) between said first (11*a*) and second (11*b*) electrical terminals, having a preset pattern as a function of said cell current ($I_p$),
   characterized by comprising:
   a transresistance block (17), coupled to said second electrical terminal (11*b*) and configured to generate a processed voltage ($V_{out}$) as a function of said cell current ($I_p$) and of said preset pattern; and
   an adder stage (16), coupled to said transresistance block (17) and to said second electrical terminal (11*b*), and configured to perform a sum between said processed voltage ($V_{out}$) and said second voltage ($V_s^-$), to generate said first voltage ($V_s^+$) for the first electrical terminal (11*a*) of said linear oxygen sensor (1), so that said biasing voltage ($\Delta V_s$) has the preset pattern as a function of the cell current ($I_p$).

2. The circuit according to claim 1, wherein said transresistance block (17) comprises:
   a current sensing stage (12), coupled to said second terminal (11*b*) and configured to generate a sense voltage ($V_{sense}$) as a function of said cell current ($I_p$); and
   a processing stage (14), coupled to said current sensing stage (12) and configured to process said sense voltage ($V_{sense}$) based on said preset pattern to generate said processed voltage ($V_{out}$).

3. The circuit according to claim 2, wherein, as the cell current ($I_p$) varies, said preset pattern envisages:
   a minimum voltage limit ($V_{min}$), for cell current ($I_p$) values below a lower threshold ($I_{pmin}$);

a maximum voltage limit ($V_{max}$), for cell current ($I_p$) values above an upper threshold ($I_{pmax}$); and between the minimum ($V_{min}$) and maximum ($V_{max}$) voltage limits, a linear ramp pattern, with a preset slope.

4. The circuit according to claim 3, wherein said processing stage (14) comprises an operational amplifier (24) having an upper saturation voltage ($Vsat_{sup}$) and a lower saturation voltage ($Vsat_{inf}$) depending on a related supply voltage ($V_{DDS}$); wherein said operational amplifier (24) has a gain (k), which is such that the processed voltage ($V_{out}$) is equal to the upper saturation voltage ($Vsat_{sup}$) for values of the cell current ($I_p$) above said upper threshold ($I_{pmax}$), and equal to the lower saturation voltage ($Vsat_{inf}$) for values of the cell current ($I_p$) below said lower threshold ($I_{pmin}$).

5. The circuit according to claim 4, wherein said operational amplifier (24) has an offset voltage ($V_{sum}$), with a value dependent on said preset pattern.

6. The circuit according to claim 4, wherein said adder stage (16) is configured to compensate the gain (k) applied by said processing stage (14) to said processed voltage ($V_{out}$), in the sum between said processed voltage ($V_{out}$) and said second voltage ($V_s^-$) on the second electrical terminal (11b) of the linear oxygen sensor (1).

7. The circuit according to claim 2, wherein said current sensing stage (12) comprises a sensing resistor (20), connected between said second electrical terminal (11b) of said linear oxygen sensor (1) and a node ($N_1$) set at a reference voltage ($V_{ref}$).

8. The circuit according to claim 1, further comprising a decoupling stage (18), connected between a sum output ($N_3$) of said adder stage (16) and said first electrical terminal (11a) of said linear oxygen sensor (1); said decoupling stage (18) being configured to receive a control signal ($S_c$), and operable based on said control signal ($S_c$) for selectively decoupling said sum output ($N_3$) from said first electrical terminal (11a), during at least one operating condition.

9. The circuit according to claim 8, wherein said operating condition is a measurement condition for measuring an operating temperature (T) of said linear oxygen sensor (1), envisaging: sending a measurement current ($I_{meas}$) between said first (11a) and second (11b) electrical terminals of said linear oxygen sensor (1); and measuring the resistance of said linear oxygen sensor (1) at the passage of said measurement current ($I_{meas}$); wherein said decoupling stage (18) is configured to decouple said sum output ($N_3$) from said first electrical terminal (11a) in a manner temporally limited to performing of said operating temperature measurement.

10. The circuit according to claim 8, wherein said decoupling stage (18) comprises at least one switch element (36a, 36b), operable by said control signal ($S_c$) to bring the sum output ($N_3$) of said adder stage (16) to a high-impedance state.

11. The circuit according to claim 8, comprising a measuring stage (19), coupled to said first (11a) and second (11b) electrical terminals of said linear oxygen sensor (1) and configured to: generate said control signal ($S_c$); provide said measurement current ($I_{meas}$) between said first (11a) and second (11b) electrical terminals of said linear oxygen sensor (1); and measure the resistance of said linear oxygen sensor (1) at the passage of said measurement current ($I_{meas}$).

12. The circuit according to claim 1, of a purely analog type.

13. An internal combustion engine (60), comprising a discharge and/or intake conduit (61), and a linear oxygen sensor (1) according to claim 1, configured to measure an oxygen concentration in the gases present in said discharge and/or intake conduit (61).

14. A control method for a single-cell linear oxygen sensor (1) having a first (11a) and a second (11b) electrical terminals on which a first voltage ($V_s^+$) and, respectively, a second voltage ($V_s^-$) are provided, wherein a cell current ($I_p$) between said first (11a) and second (11b) electrical terminals is indicative of a detected oxygen concentration, comprising the step of generating a biasing voltage ($\Delta V_s$) between said first (11a) and second (11b) electrical terminals, having a preset pattern as a function of said cell current ($I_p$), characterized in that the step of generating comprises:
generating a processed voltage ($V_{out}$) as a function of said cell current ($I_p$) and of said preset pattern; and
performing a sum between said processed voltage ($V_{out}$) and said second voltage ($V_s^-$), to generate said first voltage ($V_s^+$) for the first electrical terminal (11a) of said linear oxygen sensor (1), so that said biasing voltage ($\Delta V_s$) has the preset pattern as a function of the cell current ($I_p$).

15. The method according to claim 14, wherein said step of generating comprises:
generating a sense voltage ($V_{sense}$) as a function of said cell current ($I_p$); and
processing said sense voltage ($V_{sense}$) based on said preset pattern for generating said processed voltage ($V_{out}$).

16. The method according to claim 14, wherein said step of generating is implemented by a control circuit (10) coupled to the linear oxygen sensor (1); further comprising: selectively decoupling said first electrical terminal (11a) from said control circuit (10) during at least one operating condition, wherein said operating condition is a measurement condition for measuring an operating temperature (T) of said linear oxygen sensor (1), envisaging: sending a measurement current ($I_{meas}$) between said first (11a) and second (11b) electrical terminals of said linear oxygen sensor (1); and measuring the resistance of said linear oxygen sensor (1) at the passage of said measurement current ($I_{meas}$); wherein said step of decoupling has a duration temporally limited to performing said measurement of the operating temperature.

17. The method according to claim 16, further comprising, following said decoupling step: sending said measurement current ($I_{meas}$) between said first (11a) and second (11b) electrical terminals of said linear oxygen sensor (1); measuring the resistance of said linear oxygen sensor (1) at the passage of said measurement current ($I_{meas}$) to determine said operating temperature (T) as a function of the measured resistance; and coupling again said first electrical terminal (11a) to said control circuit (10) at the end of said operating temperature measurement.

18. The method according to claim 17, wherein a heating element (6) is coupled to the linear oxygen sensor (1); further comprising, in the case where the measurement of the operating temperature (T) is different from a preset value ($T_{des}$), the step of varying a driving condition of said heating element (6), before said step of coupling again said first electrical terminal (11a) to the control circuit (10).

19. The method according to claim 17, wherein said step of coupling again said first electrical terminal (11a) to the control circuit (10) is performed when the operating temperature (T) has a desired relationship with a preset value ($T_{des}$).

* * * * *